(12) United States Patent
Ahearn

(10) Patent No.: US 11,317,986 B1
(45) Date of Patent: May 3, 2022

(54) SAFELY SCAVENGE SCREEN ASSEMBLY

(71) Applicant: David J. Ahearn, Little Compton, RI (US)

(72) Inventor: David J. Ahearn, Little Compton, RI (US)

( * ) Notice: Subject to any disclaimer, the term of this patent is extended or adjusted under 35 U.S.C. 154(b) by 0 days.

(21) Appl. No.: 17/167,354

(22) Filed: Feb. 4, 2021

Related U.S. Application Data

(63) Continuation-in-part of application No. 16/987,592, filed on Aug. 7, 2020, now Pat. No. 11,049,626, which is a continuation of application No. 16/935,767, filed on Jul. 22, 2020.

(60) Provisional application No. 62/992,727, filed on Mar. 20, 2020.

(51) Int. Cl.
*A61B 90/00* (2016.01)
*B01D 46/10* (2006.01)
*A61L 9/20* (2006.01)

(52) U.S. Cl.
CPC .............. *A61B 90/05* (2016.02); *A61B 90/08* (2016.02); *B01D 46/10* (2013.01); *A61B 2217/005* (2013.01); *A61B 2560/04* (2013.01); *A61L 9/20* (2013.01); *H01M 2220/00* (2013.01)

(58) Field of Classification Search
CPC ..... A61B 90/05; A61B 90/08; A61B 2560/04; A61B 2217/005; A61G 10/005; A61G 13/108
See application file for complete search history.

(56) References Cited

U.S. PATENT DOCUMENTS

| | | | | |
|---|---|---|---|---|
| 2,210,370 | A * | 8/1940 | Herradora | B08B 15/04 219/147 |
| 3,537,447 | A | 11/1970 | Gauthier et al. | |
| 3,724,172 | A * | 4/1973 | Wood | A61G 10/02 95/287 |
| 4,038,913 | A * | 8/1977 | Earley | A45D 44/02 454/64 |
| 4,082,092 | A * | 4/1978 | Foster | A61M 16/009 128/847 |
| 4,446,861 | A * | 5/1984 | Tada | B08B 15/002 128/863 |
| 4,607,413 | A | 8/1986 | Schmidt et al. | |
| 4,865,049 | A | 9/1989 | Gatti | |

(Continued)

FOREIGN PATENT DOCUMENTS

| | | |
|---|---|---|
| CN | 201879716 U | 6/2011 |
| CN | 202456515 U | 10/2012 |

(Continued)

OTHER PUBLICATIONS

Hsien, et al., "Coronavirus/Taiwanese doctor creates cheap protective deice amid virus crisis," Focus Taiwan, Apr. 3, 2020, https://focustaiwan.tw/society/202003220009.

*Primary Examiner* — Adam Marcetich
(74) *Attorney, Agent, or Firm* — Adler Pollock & Sheehan P.C

(57) ABSTRACT

An apparatus includes a splash shield incorporating a clear viewing area, a vacuum manifold, the vacuum manifold adapted to releasably engage the splash shield, a light assembly removeably linked to a lower surface of the vacuum manifold, and a port emanating from the vacuum manifold, the port configured to attach to a vacuum system wherein application of a vacuum creates a laminar flow to draw vapor away from the splash shield.

11 Claims, 11 Drawing Sheets

(56) References Cited

U.S. PATENT DOCUMENTS

| | | | | |
|---|---|---|---|---|
| 4,921,492 | A * | 5/1990 | Schultz | A61M 1/008 128/888 |
| 4,936,318 | A * | 6/1990 | Schoolman | A61G 13/108 128/847 |
| 4,949,714 | A * | 8/1990 | Orr | A61G 10/04 128/200.24 |
| 5,012,852 | A | 5/1991 | Blackhurst | |
| 5,052,411 | A * | 10/1991 | Schoolman | A61B 90/40 128/863 |
| 5,122,904 | A * | 6/1992 | Fujiwara | A61B 90/25 359/510 |
| 5,336,128 | A * | 8/1994 | Birdsong | A45D 29/00 454/56 |
| 5,349,967 | A | 9/1994 | Tennis et al. | |
| 5,360,018 | A * | 11/1994 | Chen | A61B 90/05 128/846 |
| 5,636,627 | A * | 6/1997 | Rochester | A61M 16/009 128/205.27 |
| 6,076,524 | A * | 6/2000 | Corn | A61M 16/0627 128/205.12 |
| 6,119,689 | A * | 9/2000 | Korman | B01D 46/002 128/205.12 |
| 6,524,307 | B1 * | 2/2003 | Palmerton | A61B 18/00 604/22 |
| 6,663,610 | B1 * | 12/2003 | Thompson | B08B 15/00 604/313 |
| 8,684,728 | B1 | 4/2014 | Wiesemann | |
| 9,532,843 | B2 | 1/2017 | Palmerton et al. | |
| 10,420,386 | B1 | 9/2019 | Jefferis et al. | |
| 2004/0009746 | A1 * | 1/2004 | Korman | A61G 10/04 454/284 |
| 2004/0111008 | A1 * | 6/2004 | Perlatti | A61G 10/005 600/21 |
| 2004/0255937 | A1 * | 12/2004 | Sun | A61G 10/00 128/201.25 |
| 2005/0085686 | A1 * | 4/2005 | Yuen | A61G 10/005 600/21 |
| 2007/0089221 | A1 | 4/2007 | Manzella et al. | |
| 2008/0223384 | A1 * | 9/2008 | Zabari | A45D 44/00 132/73.5 |
| 2010/0081368 | A1 * | 4/2010 | Della Valle | A61G 13/108 454/66 |
| 2010/0115896 | A1 * | 5/2010 | Reid | B08B 15/04 55/356 |
| 2012/0310119 | A1 * | 12/2012 | Darder | A61H 9/005 601/6 |
| 2015/0004895 | A1 * | 1/2015 | Hammers | B08B 15/002 454/49 |
| 2015/0013783 | A1 * | 1/2015 | Palmerton | B01D 46/0036 137/356 |
| 2015/0327935 | A1 | 11/2015 | Coleman et al. | |
| 2016/0074268 | A1 * | 3/2016 | Breegi | A61G 11/009 600/21 |
| 2018/0153637 | A1 * | 6/2018 | Al-Shawi | A61B 90/40 |
| 2019/0060031 | A1 | 2/2019 | Mukherji et al. | |
| 2019/0274608 | A1 * | 9/2019 | Choi | A61B 5/150824 |
| 2020/0000541 | A1 | 1/2020 | Clemens | |
| 2020/0060375 | A1 | 2/2020 | Jascomb et al. | |
| 2020/0246103 | A1 * | 8/2020 | Szuchmacher | F21V 21/406 |

FOREIGN PATENT DOCUMENTS

| | | |
|---|---|---|
| CN | 204468120 U | 7/2015 |
| DE | 3540574 C2 | 1/1987 |
| GB | 2205501 A1 | 12/1988 |
| RU | 80336 U1 | 2/2009 |

* cited by examiner

ID# 11,317,986 B1

SAFELY SCAVENGE SCREEN ASSEMBLY

CROSS REFERENCE TO RELATED APPLICATIONS

This application is a Continuation-In-Part (CIP) application of U.S. patent application Ser. No. 16/987,592, filed Aug. 7, 2020, which is a Continuation application of U.S. patent application Ser. No. 16/935,767, filed Jul. 22, 2020, which claims benefit from U.S. Provisional Patent Application Ser. No. 62/992,727, filed Mar. 20, 2020, which are incorporated by reference in their entirety.

BACKGROUND OF THE INVENTION

The present invention relates generally to protective devices, and more particularly to a safety scavenge screen assembly.

In general, health care professionals work in close contact to patients. This is particularly true in the case of the dental profession. Given the close contact between a dentist, for example, and a patient, the potential for transmission of air born contagions from a patient suffering from a condition such as, for example, influenza or corona virus, is great. Therefore, there exists a need for a device to protect the treating medical professional from harm.

SUMMARY OF THE INVENTION

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In general, in one aspect, the invention features an apparatus a splash shield incorporating a clear viewing area, a vacuum manifold, the vacuum manifold adapted to releasably engage the splash shield, a light assembly removeably linked to a lower surface of the vacuum manifold, and a port emanating from the vacuum manifold, the port configured to attach to a vacuum system wherein application of a vacuum creates a laminar flow to draw vapor away from the splash shield.

In another aspect, the invention features an apparatus including a splash shield incorporating a clear viewing area, a vacuum manifold, the vacuum manifold adapted to releasably engage the splash shield, and a light assembly removeably linked to a lower surface of the vacuum manifold, light assembly including a lamp, a flexible neck, and a lamp base, the flexible neck linking the lamp to the lamp base.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The invention will be more fully understood by reference to the detailed description, in conjunction with the following figures, wherein.

DETAILED DESCRIPTION

Figure 1:
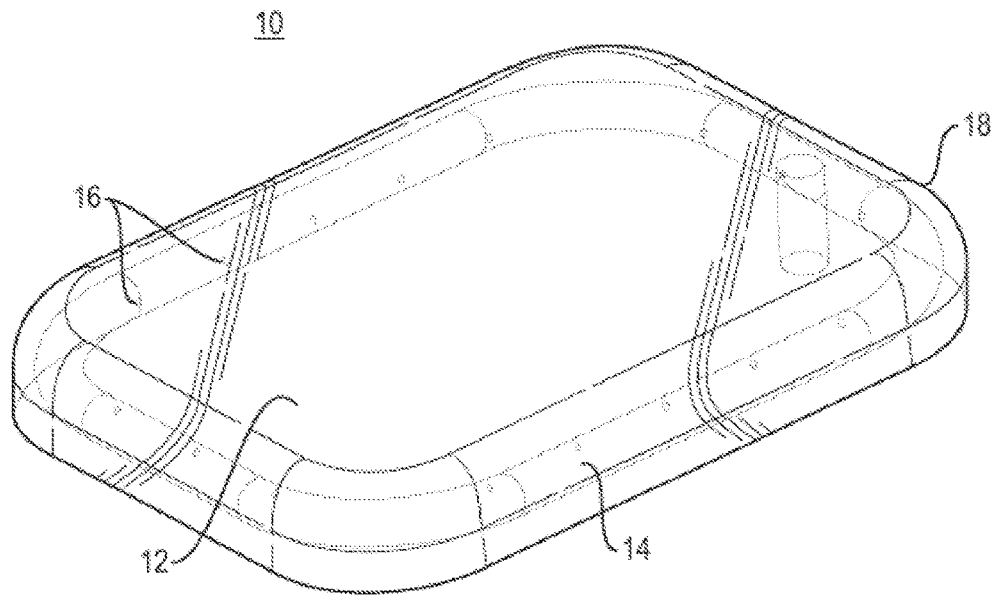
FIG. 1 is an exemplary safety scavenge screen assembly.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

In an embodiment, the present invention is an assembly that includes a removable or fixed splash shield incorporating a clear center viewing area surrounded by an evacuation collar or engaged into a vacuum manifold designed to scavenge all or the majority of patient exhalations as well as any aerosols produced during the treatment process. The apparatus is designed to be connected to a high-efficiency particulate air (HEPA) and/or ultraviolet (UV) filtration system in order to release medically disinfected exhaust. The apparatus provides an effective physical barrier between a patient and a medical caregiver.

As shown in FIG. 1, an exemplary safety scavenge screen assembly 10 includes a splash shield 12 that incorporates a viewing area. The splash shield 12 preferably is constructed of a clear plastic. In other embodiments, the splash shield 12 may be constructed of any appropriate clear material, such as glass. Affixed to a perimeter of a lower side of the splash shield 12 is an evacuation collar 14. The evacuation collar 14 may be permanently or removably attached to the lower side of the splash shield 12. When removably attached, cleaning is easily accomplished. The splash shield 12 is configured having a slightly curved main surface with a portion on its perimeter to receive and position the evacuation collar 14. In one embodiment, the evacuation collar 14 is a flexible vacuum tubing.

The evacuation collar 14 includes a number of intake orifices 16. The evacuation collar 14 also includes a link 18. The link 18 is used to connect the evacuation collar 14 to a vacuum system that preferably includes a high-efficiency particulate air (HEPA) and/or ultraviolet (UV) filtration system (not shown). When a vacuum is applied, air on an underside of the splash shield 12 is drawn through the intake orifices 16 in the evacuation collar 14, out the link 18 and through the HEPA and/or UV filtration system in order to release medically disinfected exhaust. The safety scavenge screen assembly 10 provides an effective physical barrier between a patient and a medical caregiver.

Figure 2:
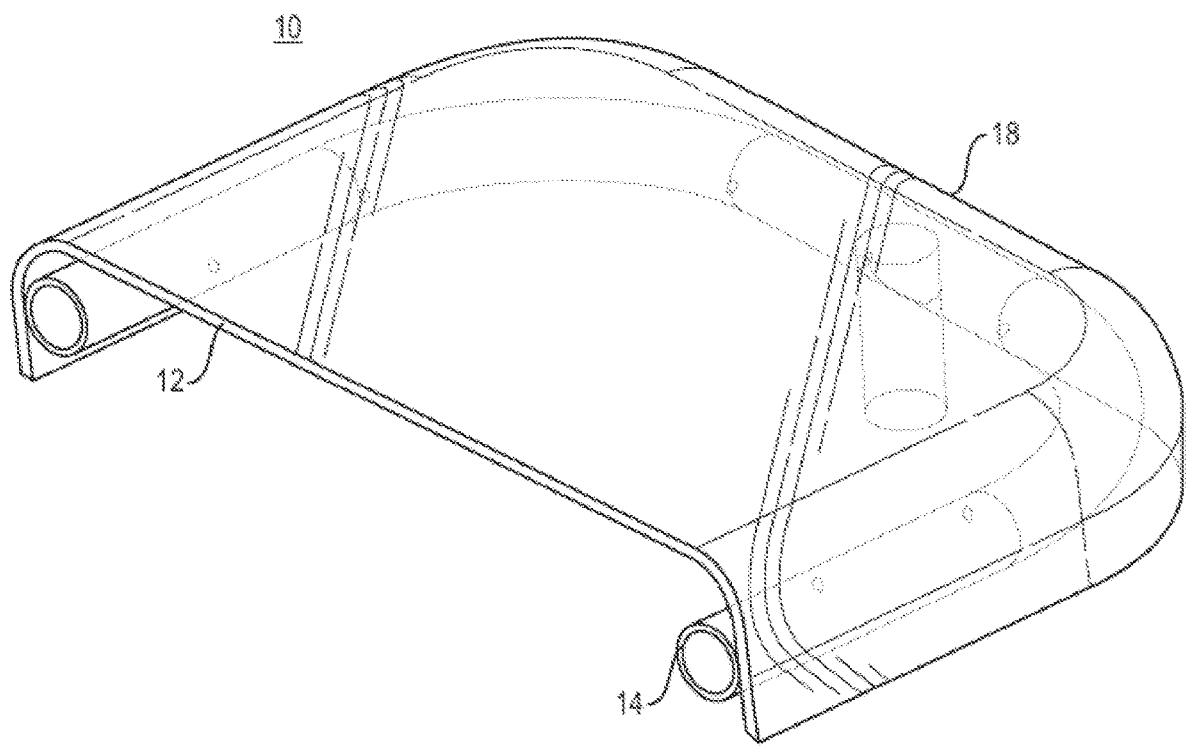
FIG. 2 is a cross section of the exemplary safety scavenge screen assembly.

In FIG. 2, a cross section of the exemplary safety scavenge screen assembly 10 of FIG. 1 is illustrated. In this illustration, edges of the splash shield 12 are more clearly shown to overlap the evacuation collar 14.

Figure 3:
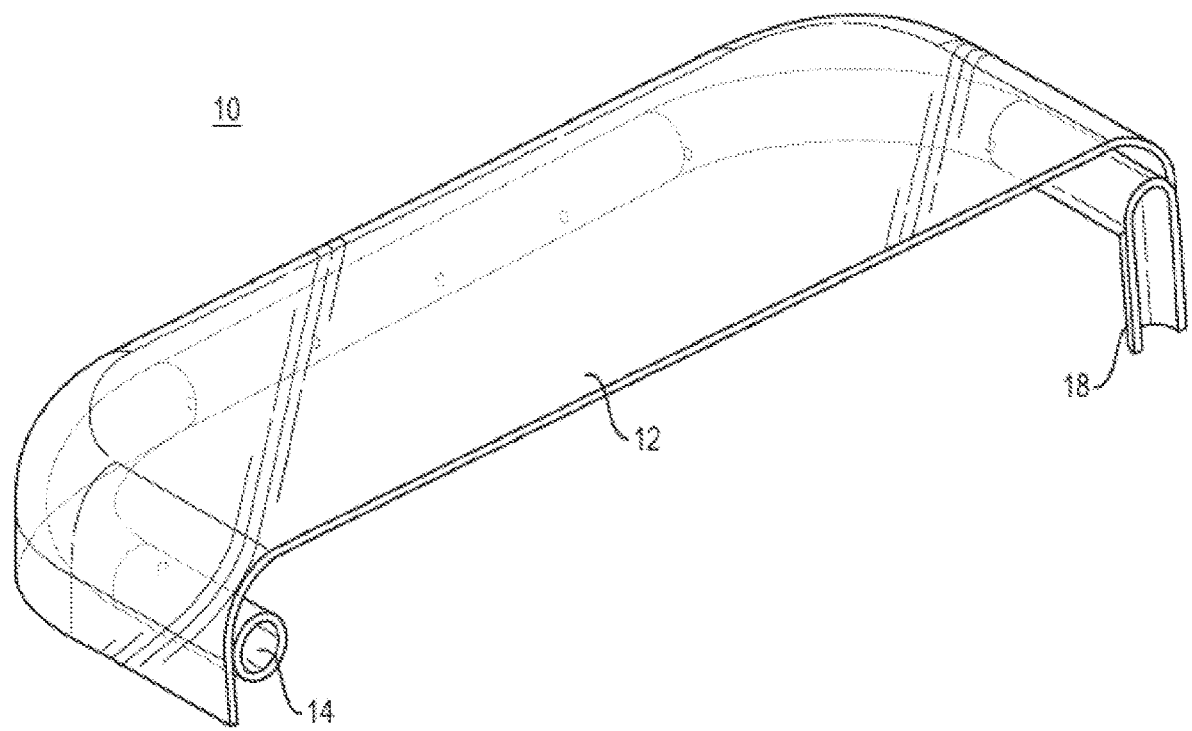
FIG. 3 is another cross section of the exemplary safety scavenge screen assembly.

In FIG. 3, another cross section of the exemplary safety scavenge screen assembly 10 of FIG. 1 is illustrated. In this illustration, the link 18, which is used to connect to a vacuum system, is more clearly shown.

Figure 4:
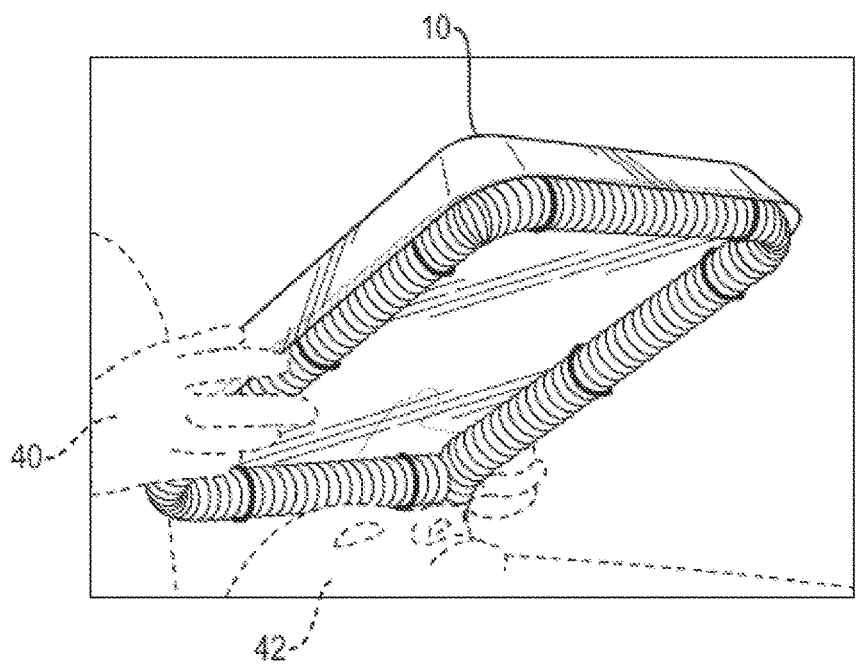
FIG. 4 illustrates an exemplary handheld positioning of the safety scavenge screen assembly about a patient.

As shown in FIG. 4, the safety scavenge screen assembly 10 may be manually positioned and held by a caregiver 40 over a patient 42. Exhalations from the patient 42 are drawn away from the caregiver 40 when vacuum is applied to the safety scavenge screen assembly 10, protecting the caregiver 40 and the surrounding environment from potential air born contagions emanating from the patient 42.

Figure 5:
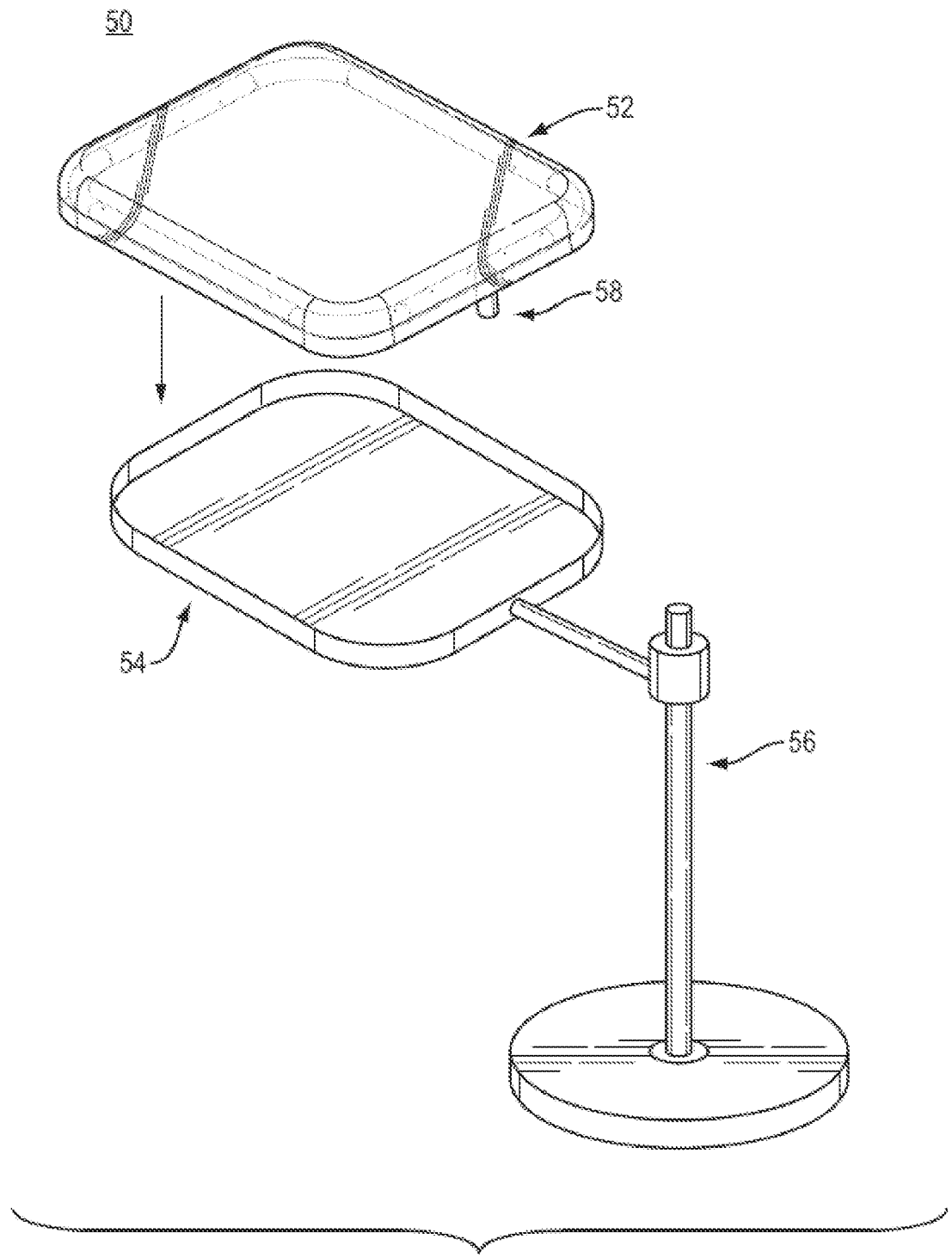
FIG. 5 is an exemplary system including an adjustable stand.

As shown in FIG. 5, an exemplary system 50 includes a safety scavenge screen assembly 52 and an assembly holder 54 connected to an adjustable stand 56. The safety scavenge screen assembly 52 may be removably placed within the assembly holder 54. Placement of the scavenge screen assembly 52 in the assembly holder 54 connected to the adjustable stand 56 enables a caregiver to modify/adjust a height and/or orientation of the safety scavenge screen assembly 52 with respect to a patient undergoing treatment. Connection of a vacuum system (not shown) to the vacuum connection 58 of the safety scavenge screen assembly 52 enables removal of potential air born contagions emanating from the patient 42.

Figure 6:
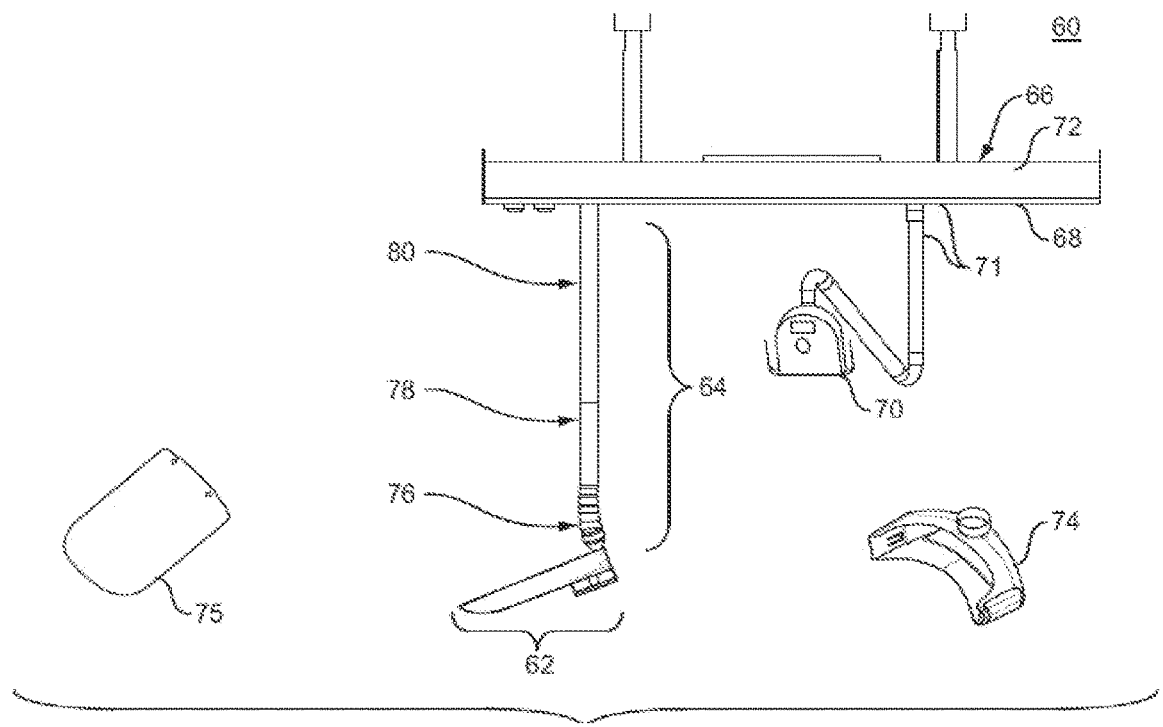
FIG. 6 is an exemplary overhead system.

A shown in FIG. 6, an exemplary overhead mounted system 60 includes a safety scavenge screen assembly 62 linked to an articulating arm 64 of a ceiling assembly 66. The articulating arm 64 may be moved in any one of three dimensions. The articulating arm 64 slides along a trolley 68 within the ceiling assembly 66 enabling the safety scavenge screen assembly 62 to be placed in multiple positions about a patient (not shown). The system 60 also may include a lighting device and/or camera 70 linked to the trolley 68 with an articulating arm 71. The ceiling assembly 66 may also include one or more lights 72 to provide illumination. Connection of a vacuum system (not shown) to a manifold 74 of the safety scavenge screen assembly 62 enables removal of potential air born contagions emanating from the patient. In the embodiment shown, the articulating arm 64 includes flex collars 76, an adjustable extrusion 78 and a downtube extrusion 80.

Figure 7:
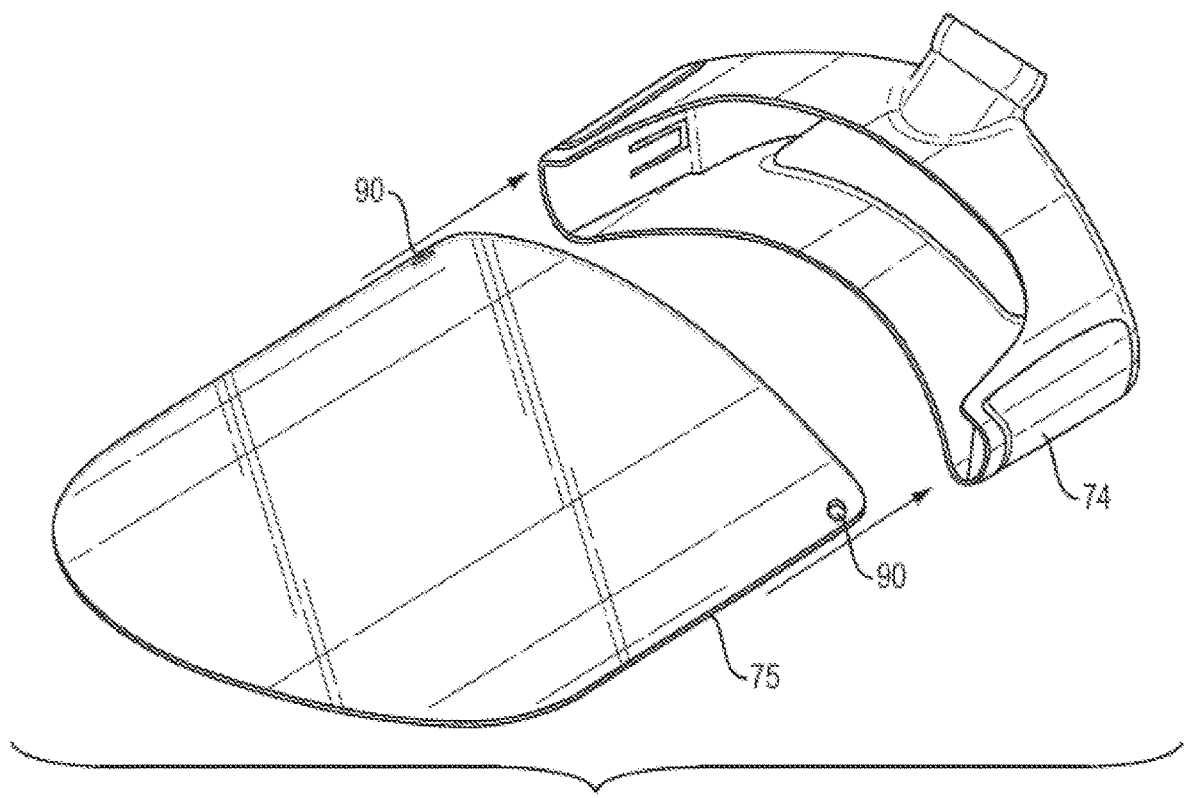
FIG. 7 is an exemplary detached safety scavenge screen assembly.

In FIG. 7, an exemplary safety scavenge screen assembly 62 includes a slightly curved face shield 75 that is configured to be removably secured to a manifold 74. In one specific implementation, the face shield 75 is 20¾ inches in length, 14¾ inches width and has a curve radius of 15 inches. These example measurements include a tolerance of +/−0.25 inches.

Figure 8:
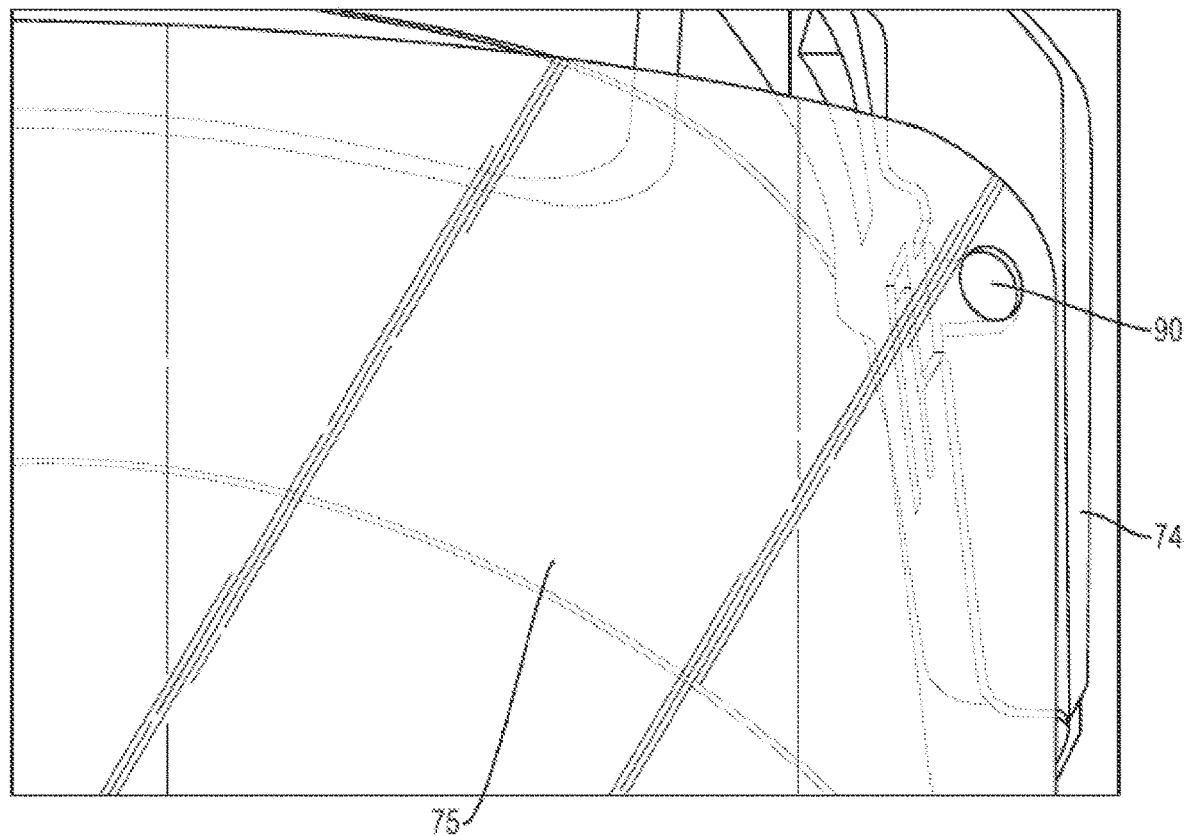
FIG. 8 is an exemplary safety scavenge screen assembly

As shown in FIG. 8, the face shield 75 includes slots 90 along its side walls that are designed to engage and lock in corresponding receptacles 92 in the side walls of the manifold 74.

Figure 9:
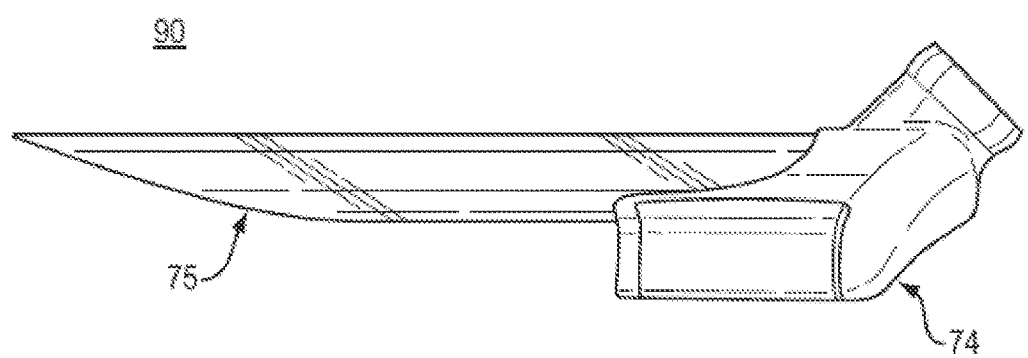
FIG. 9 is an exemplary safety scavenge screen assembly.

As shown in FIG. 9, when the face shield 75 is engaged within the manifold 74 and vacuum is applied, the manifold 74 creates a laminar flow to draw vapor away from a medical care provider and is best described as a linear pull design. This linear pull design enables an ability to capture and hold two to four times an adult patient's tidal volume until such time it is carried away by the manifold 74. This excess volume is available to capture extreme events such as a patient's cough, sneeze or even vomit in the case of intubating physicians. Thus, the safety scavenge screen assembly 90 provides an effective physical barrier between a patient and the medical caregiver.

Figure 10:
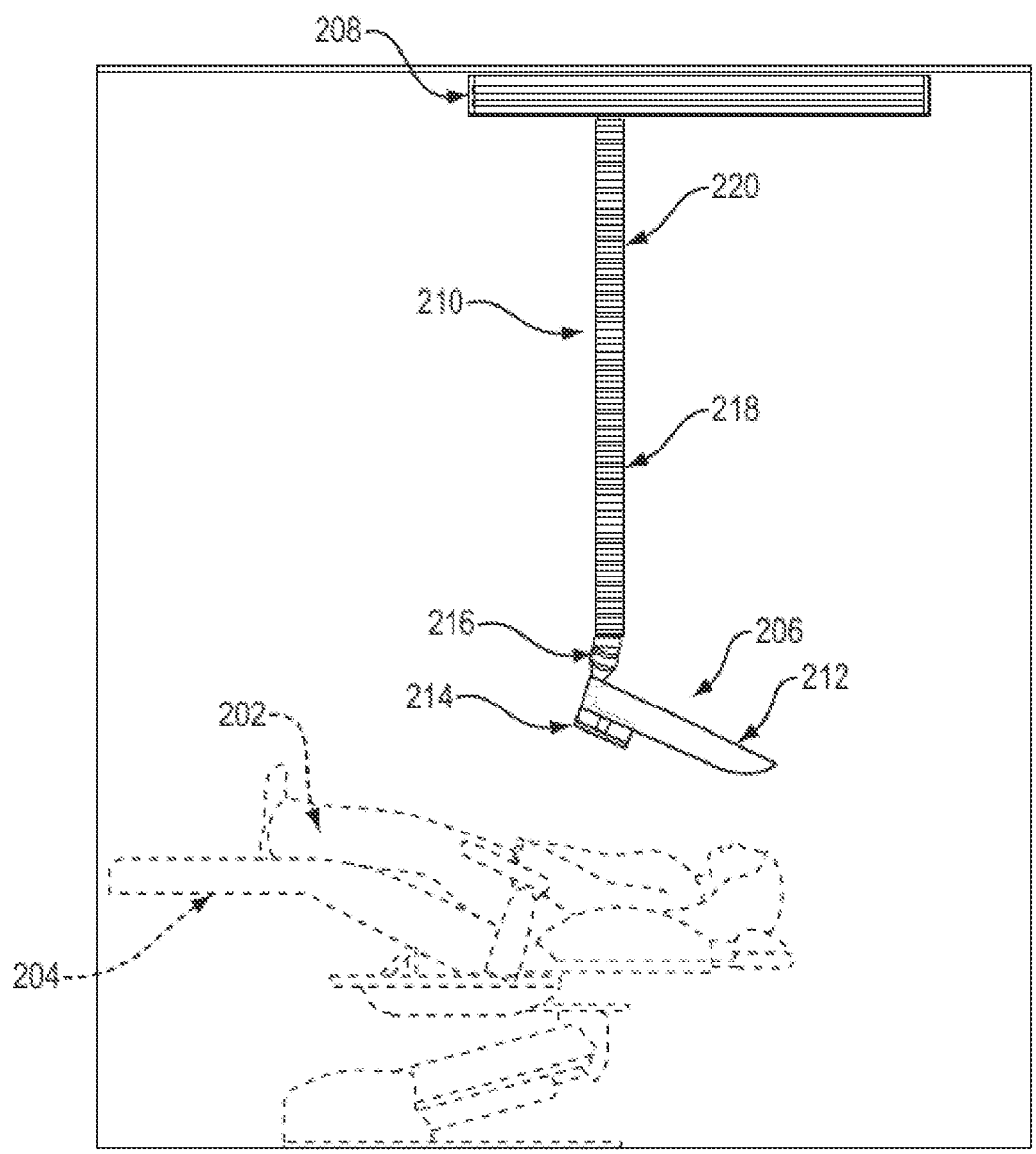
FIG. 10 is an exemplary examination room.

As shown in FIG. 10, an exemplary examination room 200 includes a patient 202 reclining on an examination chair 204. A safety scavenge screen assembly 206 is linked to an overhead trolley 208 with an articulating arm 210. The safety scavenge screen assembly 206 includes a removable face shield 212 engaged to a manifold 214. In one implementation, the manifold 214 in linked to a vacuum system (not show) within the articulating arm 210. In another implementation, a vacuum system (not shown) is linked directly to the manifold 214. The articulating arm 210 includes a collar 216, a extension tube 218 and a fixed tube 220.

Figure 11:
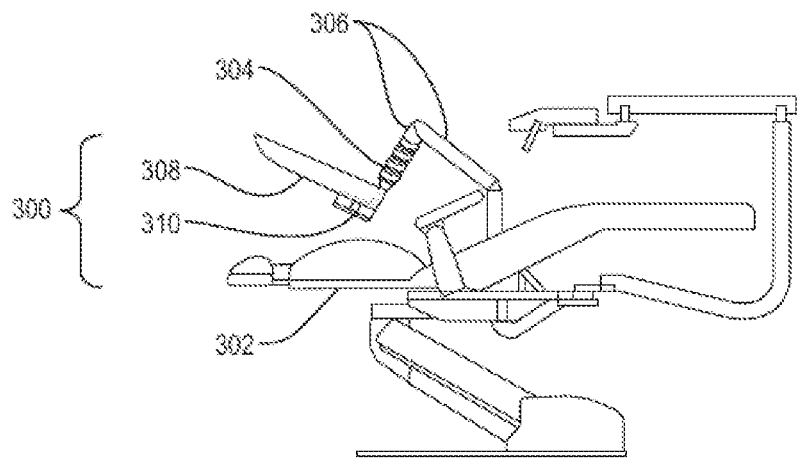
FIG. 11 is an exemplary safety scavenge screen assembly affixed to an examination chair.

As shown in FIG. 11, a safety scavenge screen assembly 300 is affixed to an examination chair 302 with flex collars 304 and articulating arms 306, both of which enable positioning of the safety scavenge screen assembly 300 in three dimensions. As described above, the safety scavenge screen assembly 300 includes a removable face shield 308 engaged in a manifold 310. The manifold 310 is adapted to link to a vacuum system (not shown) directly or through a vacuum hose positioned within the flex collars 304 and articulating arms 306.

Figure 12:
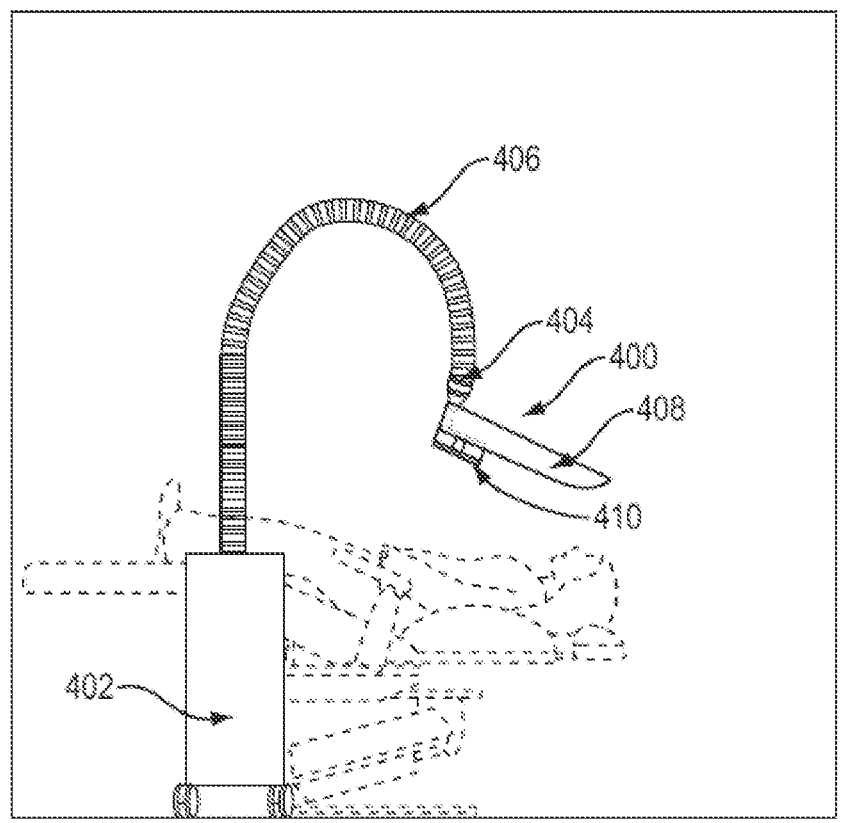
FIG. 12 is an exemplary safety scavenge screen assembly affixed to a stationary or mobile cart.

As shown in FIG. 12, a safety scavenge screen assembly 400 is affixed to a stationary or mobile cart 402 with flex collars 404 and articulating arms 406, both of which enable positioning of the safety scavenge screen assembly 300 in three dimensions. As described above, the safety scavenge screen assembly 400 includes a removable face shield 408 engaged in a manifold 410. The manifold 410 is adapted to link to a vacuum system (not shown) directly or through a vacuum hose positioned within the flex collars 404 and articulating arms 406.

Figure 13:
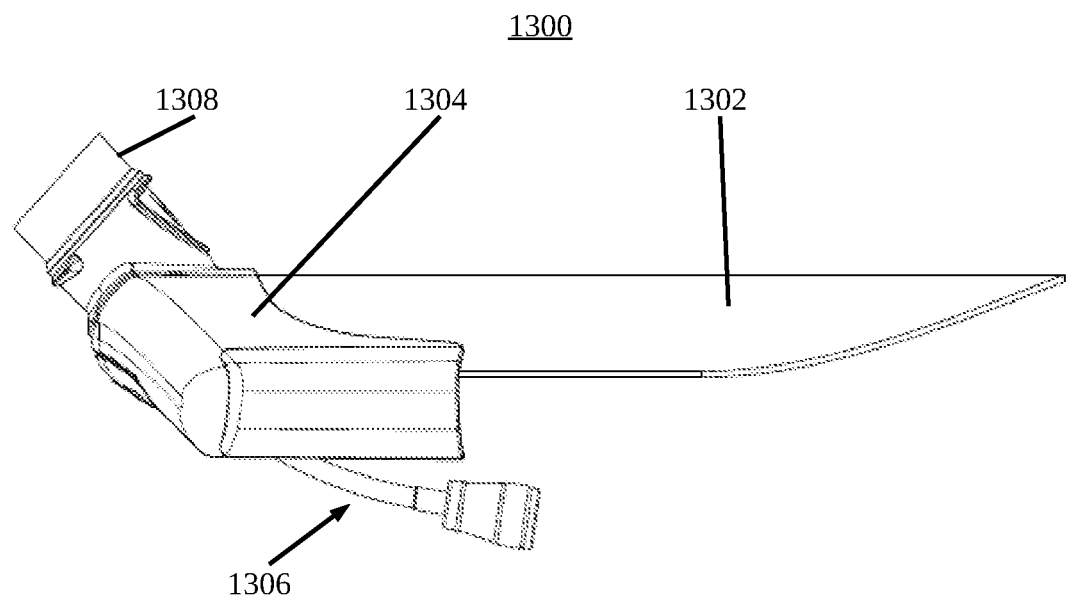
FIG. 13 is a side view of another embodiment of an exemplary safety scavenge screen assembly.

In FIG. 13, a side view of another embodiment of an exemplary safety scavenge screen assembly 1300 includes a removable shield assembly 1302 releasably linked to a manifold assembly 1304. In addition, a removable light assembly 1306 is shown secured to the manifold assembly 1304. As described above, the removable shield assembly 1302 is constructed of a clear material, such as a clear plastic or glass, which provides a clear viewing area. The manifold assembly 1304 includes a port 1308 designed to engage a vacuum system (not shown). Here, the removable light assembly 1306 provides variable lighting below the removable shield assembly 1302.

Figure 14:
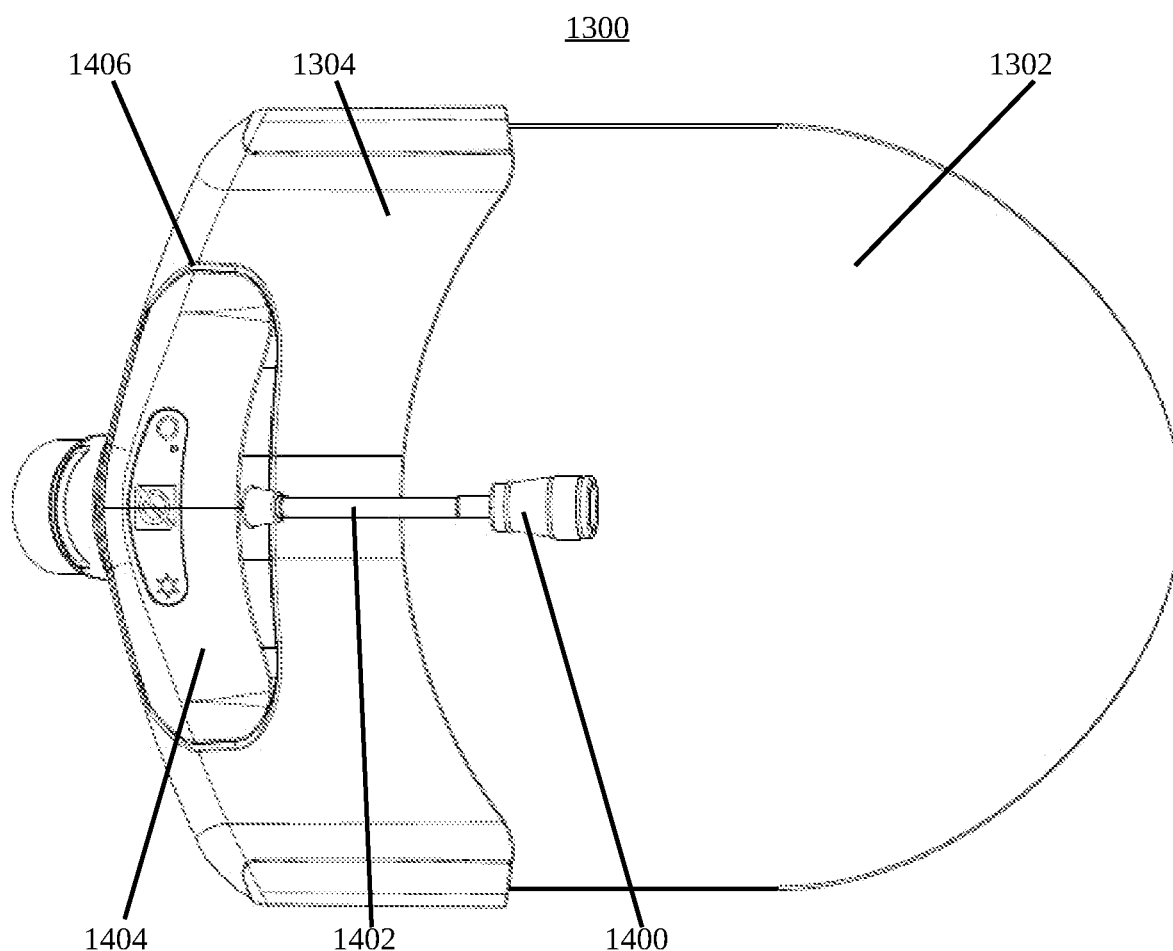
FIG. 14 is a bottom view of the exemplary safety scavenge screen assembly of FIG. 13.

In FIG. 14, a bottom view of the safety scavenge screen assembly 1300 illustrates positioning of the removable light assembly 1306 within a lower portion of the manifold assembly 1304. Here, the removable light assembly 1306 includes a lamp 1400, a flexible neck 1402 and a lamp base 1404. The flexible neck 1402 enables multi-directional positioning of the lamp 1400. Although not shown, the lamp base 1404 may includes a connection to an external power supply, such as an AC/DC circuit. In other embodiments, the lamp base 1404 may include a battery power source, which may or may not be rechargeable. The lamp base 1404 is releasably affixed in a manifold assembly receptacle 1406.

Figure 15:
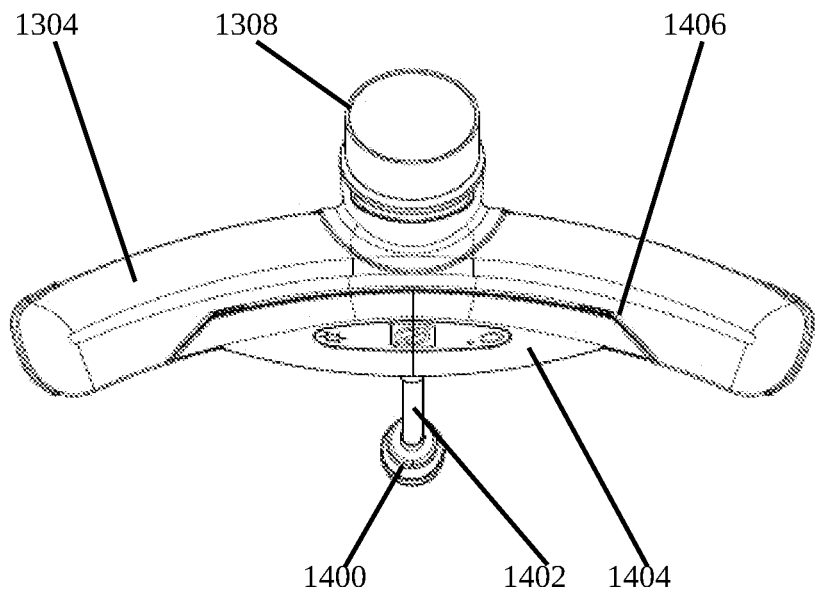
FIG. 15 a rear view of the lamp base inserted within the assembly receptacle.

In FIG. 15, a rear view of the lamp base 1404 inserted within the assembly receptacle 1406 is illustrated.

Figure 16:
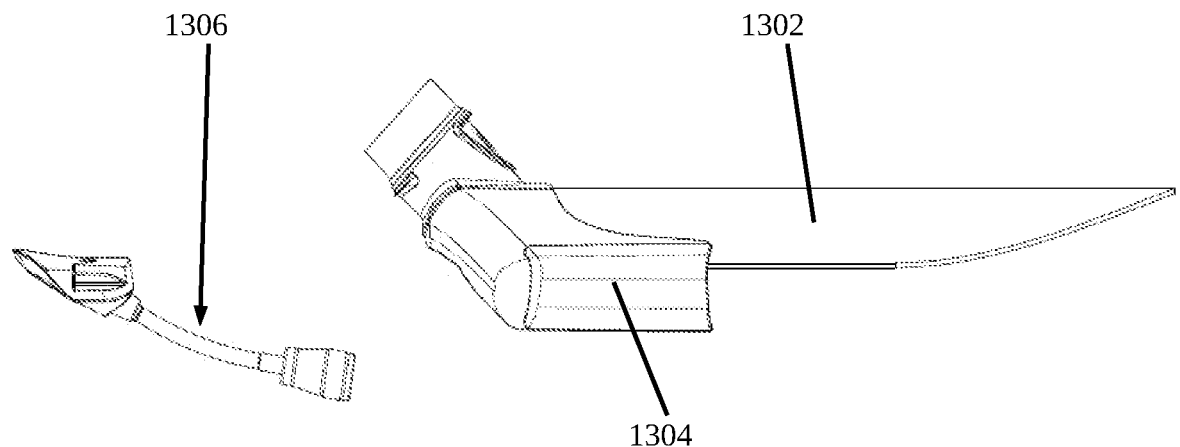
FIG. 16 illustrates a side view of the light assembly separated from the manifold assembly.

FIG. 16 illustrates a side view of the light assembly 1306 separated from the manifold assembly 1304. Here, the shield assembly 1302 is shown locked into the manifold assembly 1304.

Figure 17:
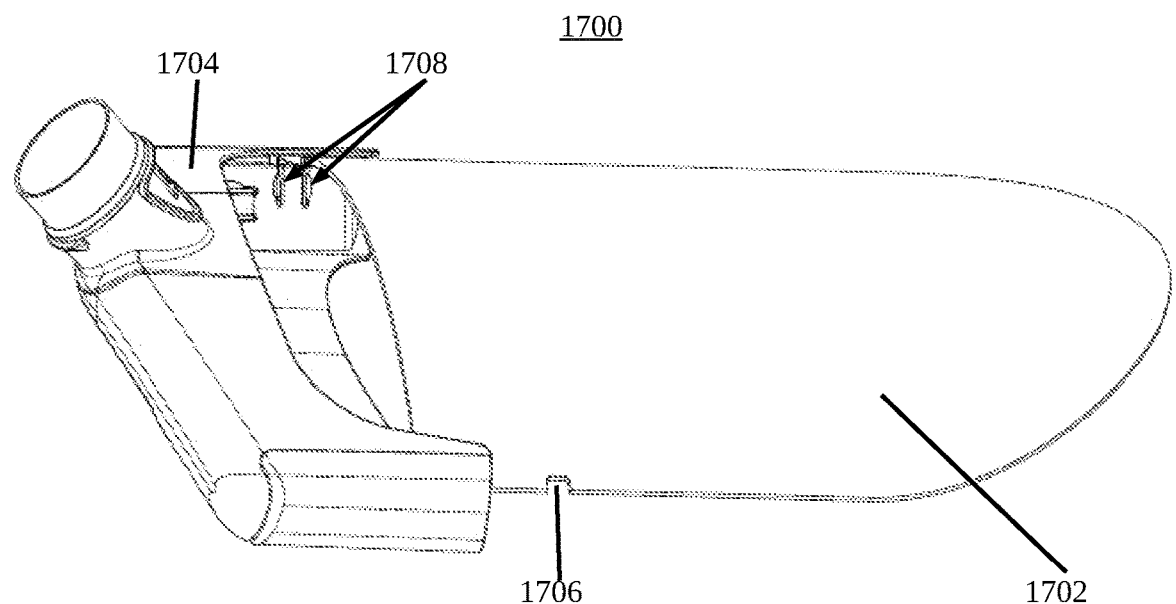
FIG. 17 and FIG. 18 illustrate an exemplary safety scavenge screen assembly.
Figure 18:
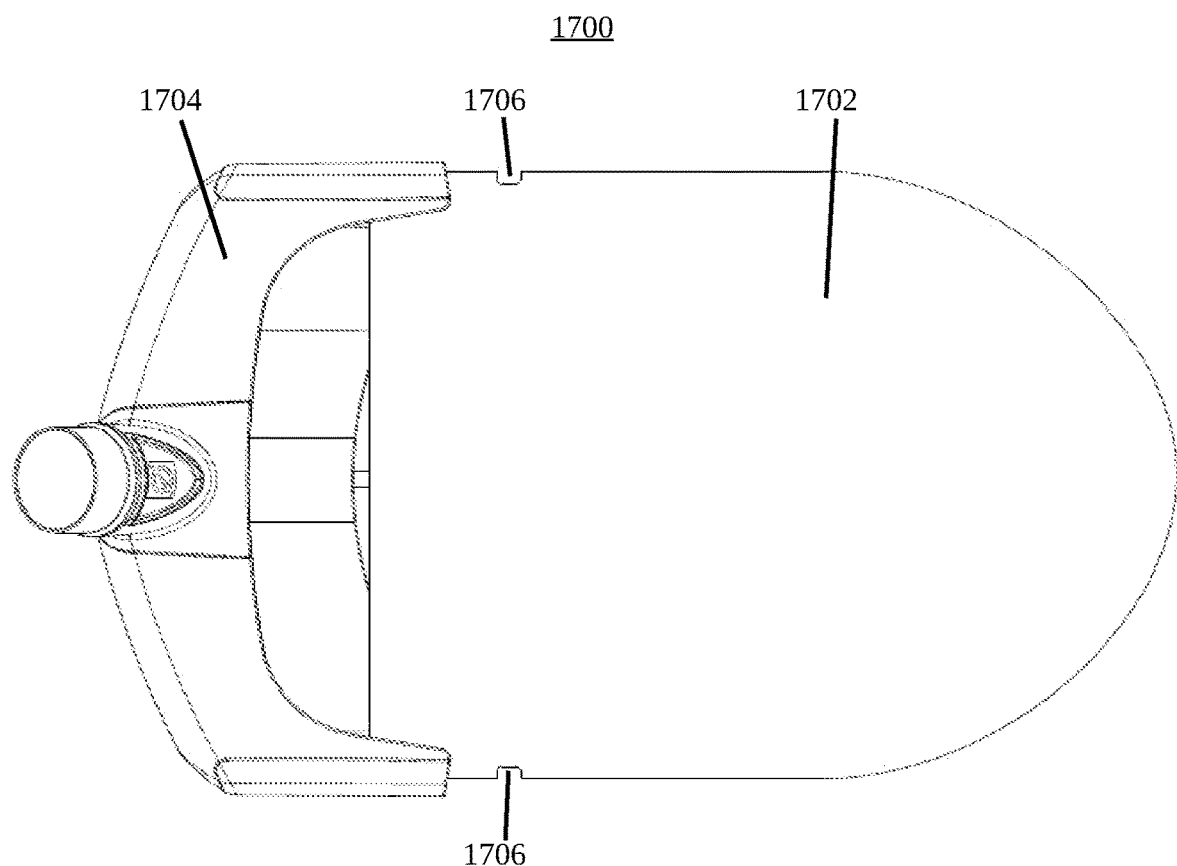

As shown in FIG. 17 and FIG. 18, an exemplary safety scavenge screen assembly 1700 includes a removable shield assembly 1702 positioned adjacent to a manifold assembly 1704. Here, the shield assembly 1702 includes posterior indents 1706 along its perimeter that when the shield assembly 1702 is positioned in the manifold assembly 1704 engage corresponding detents 1708 in a side wall of the manifold assembly 1704. The detents 1708 are catches in the manifold assembly 1704 that enable a locking of the shield assembly 1702 into the manifold assembly 1704. When the detents 1708 are depressed, the shield assembly 1702 may be released from the manifold assembly 1704.

Figure 19:
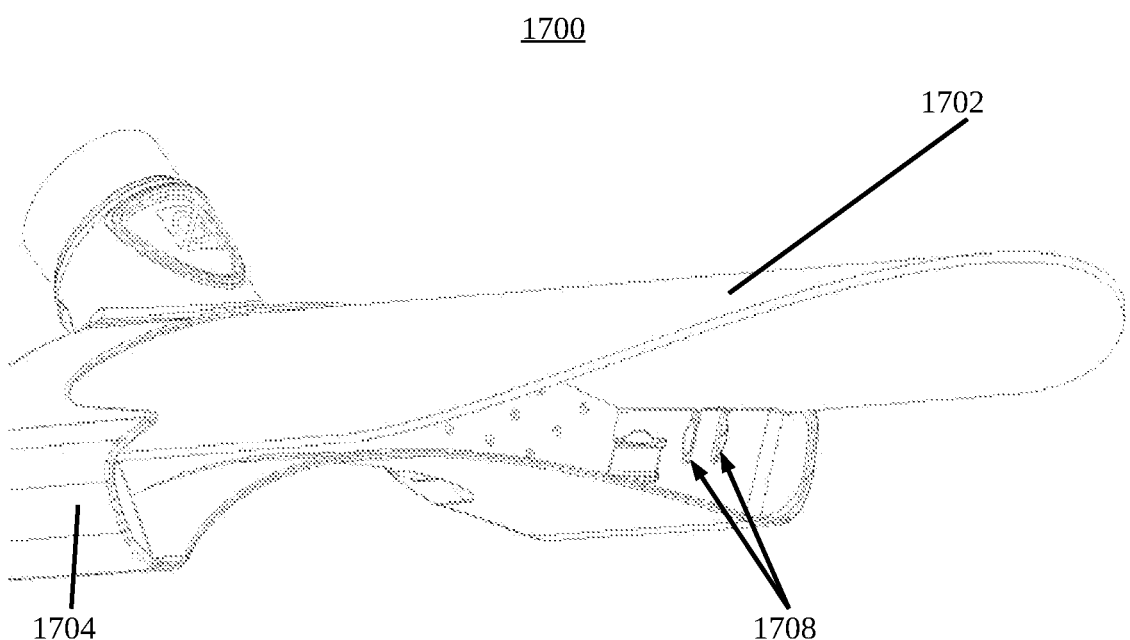
FIG. 19 illustrates a side prospective of the removable shield assembly positioned over the detents to a manifold assembly.

In FIG. 19, a side prospective of the removable shield assembly 1702 positioned over the detents 1708 to a manifold assembly 1704 is illustrated.

It would be appreciated by those skilled in the art that various changes and modifications can be made to the illustrated embodiments without departing from the spirit of the present invention. All such modifications and changes are intended to be within the scope of the present invention except as limited by the scope of the appended claims.

What is claimed is:

1. An apparatus comprising:
a splash shield incorporating a clear viewing area;
a vacuum manifold, the vacuum manifold adapted to releasably engage the splash shield;
a light assembly removably linked to a lower surface of the vacuum manifold; and
a port emanating from the vacuum manifold, the port configured to attach to a vacuum system wherein application of a vacuum creates a laminar flow to draw vapor away from the splash shield,
wherein the splash shield comprises posterior indents along its perimeter that engage corresponding detents in a side wall of the manifold assembly.

2. An apparatus comprising:
a splash shield incorporating a clear viewing area;
a vacuum manifold, the vacuum manifold adapted to releasably engage the splash shield;
a light assembly removably linked to a lower surface of the vacuum manifold;
a port emanating from the vacuum manifold, the port configured to attach to a vacuum system wherein application of a vacuum creates a laminar flow to draw vapor away from the splash shield,
wherein the light assembly comprises:
a lamp;
a flexible neck; and
a lamp base, the flexible neck linking the lamp to the lamp base.

3. The apparatus of claim 2 wherein the lamp base includes a power supply connection.

4. The apparatus of claim 2 wherein the lamp base includes a battery.

5. The apparatus of claim 4 wherein the battery is rechargeable.

6. An apparatus comprising:
a splash shield incorporating a clear viewing area;
a vacuum manifold, the vacuum manifold adapted to releasably engage the splash shield;
and a light assembly removably linked to a lower surface of the vacuum manifold, the light assembly comprising a lamp, a flexible neck, and a lamp base, the flexible neck linking the lamp to the lamp base.

7. The apparatus of claim 6 wherein vacuum manifold includes a port configured to attach to a vacuum system wherein application of a vacuum creates a laminar flow to draw vapor away from the splash shield.

8. The apparatus of claim 6 wherein the splash shield comprises posterior indents along its perimeter that engage corresponding detents in a side wall of the manifold assembly.

9. The apparatus of claim 6 wherein the lamp base includes a power supply connection.

10. The apparatus of claim 9 wherein the lamp base includes a battery.

11. The apparatus of claim 10 wherein the battery is rechargeable.

* * * * *